United States Patent [19]

Shinohara et al.

[11] Patent Number: 4,659,852

[45] Date of Patent: Apr. 21, 1987

[54] 4-CHLOROMETHYLPHENYL METHYL DICHLOROSILANE

[75] Inventors: Toshio Shinohara; Masahiko Ogawa; Akio Yokoo, all of Gunma, Japan

[73] Assignee: Shin-Etsu Chemical Co., Ltd., Tokyo, Japan

[21] Appl. No.: 909,101

[22] Filed: Sep. 18, 1986

[30] Foreign Application Priority Data

Sep. 19, 1985 [JP] Japan ................................ 60-207153

[51] Int. Cl.$^4$ .............................................. C07F 7/08
[52] U.S. Cl. ..................................... 556/476; 556/488
[58] Field of Search ................................ 556/476, 488

[56] References Cited

U.S. PATENT DOCUMENTS 2,803,638  8/1957  Holdstock ........................... 556/476
3,449,393  6/1969  Sattlegger et al. .................. 556/476
3,929,851  12/1975  Heathcote et al. ............. 556/476 X Primary Examiner—Paul F. Shaver
Attorney, Agent, or Firm—Toren, McGeady and Goldberg

[57] ABSTRACT

The inventive compound 4-chloromethylphenyl methyl dichlorosilane is a novel compound not known in the prior art. The silane compound can readily be prepared by the chlorination of 4-tolyl methyl dichlorosilane with sulfuryl chloride as the chlorinating agent. The novel silane compound is useful as a component of an organochlorosilane mixture as the starting material of various kinds of silicone products or, in particular, silicone resins capable of exhibiting high performance, e.g. sensitivity for radiation-induced curing, not obtained by any combinations of known organochlorosilanes.

2 Claims, No Drawings

4-CHLOROMETHYLPHENYL METHYL DICHLOROSILANE

BACKGROUND OF THE INVENTION

The present invention relates to 4-chloromethylphenyl methyl dichlorosilane, which is a novel organosilicon compound not known in the prior art or not described in any printed publications.

As is well known, the starting materials of silicone resins or, generally, silicone products are various kinds of organochlorosilanes. Methyl chlorosilanes and phenylchlorosilanes as the typical classes of the organochlorosilanes are produced by the so-called "direct method", in which metallic silicon in a powdery form is reacted with methyll chloride or chlorobenzene in the presence of powdery copper as the catalyst to give a mixture of methyl chlorosilanes or mixture of phenyl chlorosilanes. When a different kind of the hydrocarbon group bonded to the silicon atom of the silane is desired by introducing into an organochlorosilane as in the preparation of methyl phenyl dichlorosilane from methyl trichlorosilane, a Grignard process is applicable. Namely, for example, methyl trichlorosilane is reacted with phenyl magnesium chloride, i.e. the Grignard reagent of chlorobenzene to replace one of the chlorine atoms in the methyl trichlorosilane with a phenyl group. A great variety of organochlorosilanes are being industrially produced by the combinations of the "direct method" and the Grignard reaction and are used as the starting materials for the preparation of silicone products.

Namely, the silicone products or, in particular, silicone resins are produced by the (co)hydrolysis of an organochlorosilane or a mixture of two kinds or more of organochlorosilanes followed by the polycondensation between the silanol groups formed by the hydrolysis of the silicon-bonded chlorine atoms. Accordingly, the most fundamental key factor influencing the properties of the silicone product is the kinds and combination of the starting organochlorosilanes and the intensively continued investigations conducted in this connection in the technology of silicones for many years have exhaustively developed the possibility of obtaining a new silicone product to meet the requirements for a material useful in modern high-technologies.

For example, the application fields of silicone resins are rapidly expanding in the electronics and other high-technologies with requirements for the silicone products to have higher and higher improved properties. Notwithstanding the requirements in the application fields, it is a general impression in the silicone technology that great improvements in the properties of new silicone products over the existing ones can hardly be expected or a limitation is being approached insofar as the organochlorosilanes as the starting materials of the silicone products are selected among known ones having relatively simple molecular structures. Taking a silicone-based photoresist resin used in the processing of semiconductor devices as an example, it is eagerly desired to develop a silicone resin having a structure susceptible to photo-induced decomposition or crosslinking in a molecule and still having high resistance against heat and the conditions of etching. The inventors also continued investigations on this problem only to be led to a conclusion that no combination of conventional methyl chlorosilanes and phenylchlorosilanes as well as other known organochlorosilanes could provide a possibility of obtaining a novel silicone resin product to meet the requirements in the modern applicaiton fields. Therefore, it is one of the important ways of investigations in the technology of silicones to discover a novel organochlorosilane compound useful as a starting material of high-performance silicone resins.

SUMMARY OF THE INVENTION

Thus, the principal object of the present invention is to provide a novel organochlorosilane having a possibility of being used as a starting material of high-performance silicone resins. The invention also has an object to provide an efficient method for the preparation of such a novel organochlorosilane compound.

The novel organochlorosilane compound of the invention discovered as a result of the investigations undertaken with the above mentioned objects is 4-chloromethylphenyl methyl dichlorosilane expressed by the structural formula

$(ClCH_2-C_6H_4)(CH_3)SiCl_2$.

This compound can readily be synthesized by the chlorination reaction of 4-tolyl methyl dichlorosilane, which is synthesized by the Grignard reaction of methyl trichlorosilane with 4-tolylmagnesium chloride, with sulfuryl chloride as the chlorinating agent.

DETAILED DESCRIPTION OF THE PREFERRED EMBODIMENTS

Although the inventive compound, viz. 4-chloromethylphenyl methyl dichlorosilane, can be synthesized in various synthetic routes, the investigation undertaken by the inventors have led to a conclusion that the most efficient route is the above described method by the chlorination of 4-tolyl methyl dichlorosilane with sulfuryl chloride as the chlorinating agent. This route of the synthesis can be expressed by the following reaction equations:

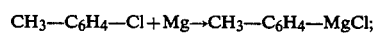

$CH_3-C_6H_4-Cl+Mg \rightarrow CH_3-C_6H_4-MgCl$;

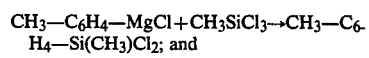

$CH_3-C_6H_4-MgCl+CH_3SiCl_3 \rightarrow CH_3-C_6H_4-Si(CH_3)Cl_2$; and

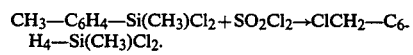

$CH_3-C_6H_4-Si(CH_3)Cl_2+SO_2Cl_2 \rightarrow ClCH_2-C_6H_4-Si(CH_3)Cl_2$.

The inventive 4-chloromethylphenyl methyl dichlorosilane can be used as a component of an organochlorosilane mixture to be subjected to cohydrolysis for the preparation of a silicone product. For example, the cohydrolysis and cocondensation reaction of a silane mixture composed of the inventive silane coompound, i.e. 4-chloromethylphenyl trichlorosilane, and methyl trichlorosilane can lead to a novel silicone resin expressed by the unit formula

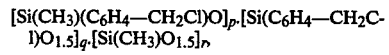

$[Si(CH_3)(C_6H_4-CH_2Cl)O]_p \cdot [Si(C_6H_4-CH_2Cl)O_{1.5}]_q \cdot [Si(CH_3)O_{1.5}]_r$, in which p, q and r are each a positive integer. This organopolysiloxane resin has an outstandingly high glass transition point and is capable of forming a uniform film. The resin is useful as a material of resist capable of being used under irradiation with high energy radiations since the organopolysiloxane contains chloromethyl groups exhibiting high sensitivity to the irradiation with high energy radiations such as electron beams and still is highly resistant against gaseous plasma of carbon tetrachloride and carbon tetrafluoride by virtue of the aromatic rings and against gaseous plasma of oxygen by virtue of the siloxane linkages in the molecular structure.

In the following, a description is given to illustrate the synthetic procedure and charactaerization of the inventive 4-chloromethylpyhenyl methyl dichlorosilane in more detail along with a description of an organopolysiloxane resin prepared with the inventive silane compound as a component of the starting organochlorosilane mixture.

EXAMPLE 1

Into a four-necked, round-bottom flask of 5-liters capacity equipped with a stirrer, reflux condenser, thermometer and dropping funnel were introduced 616 1 g (3 moles) of tolyl methyl dichlorosilane and 608 g (4.5 moles) of sulfuryl chloride to form a uniform reaction mixture. After replacement of the air inside the flask with nitrogen gas, 0.5 g of benzoyl peroxide was added to the reaction mixture as a catalyst and the temperature of the mixture was gradually increased up to 65° to 70° C., where heating of the mixture was continued for 5 hours under reflux followed by cooling to room temperature.

The reaction mixture was transferred to an equipment for distillation and subjected to distillation first to remove the unreacted sulfuryl chloride and then distillation under reduced pressure to give 521 g of a fraction boiling at 91° to 92° C. under a pressure of 1 mmHg. This fraction was identified to be a single compound by the gas chromatography and the infrared absorption spectrum thereof indicated strong absorption bands at 800 $cm^{-1}$ and 1260 $cm^{-1}$ which could be assigned to the Si—$CH_3$ groups. Further, the results of the elementary analysis and the NMR absorption spectroscopy shown below supported that this product was the desired 4-chloromethylphenyl methyl dichlorosilane.

| Results of elementary analysis | | | | |
|---|---|---|---|---|
| | C | H | Cl | Si |
| Found, % | 39.8 | 3.7 | 44.7 | 11.9 |
| Calculated as $C_8H_9Cl_3Si$, % | 40.1 | 3.8 | 44.4 | 11.7 |

| NMR absorption spectroscopic data: (ppm) | |
|---|---|
| δ 1.06 | (s,3H Si—$CH_3$) |
| δ 4.51 | (s,2H —$C_6H_4$—$CH_2Cl$) |
| δ 7.39 | (d,2H aromatic) |
| δ 7.63 | (d,2H aromatic) |

EXAMPLE 2

A solution of 144 g of 4-chloromethyl methyl dichlorosilane prepared in Example 1, 52 g of 4-chloromethylphenyl trichlorosilane and 30 g of methyl trichlorosilane in 500 g of trichloroethylene was added dropwise into 200 g of water in a flask kept at 50° to 70° C. over a period of about 2 hours under agitation. The aqueous layer was discarded and the trichloroethylene solution was neutralized and washed with water followed by stripping of trichloroethylene by distillation. The residual mixture was heated for 8 hours at 140° to 150° C. o to effect polymerization and then diluted by adding 150 g of xylene to give a silicone varnish having a viscosity of about 200 centistokes at 25° C. and containing about 50% by weight of non-volatile matter. The content of the chloromethylphenyl groups in the organopolysiloxane as the principal ingredient of the varnish was about 50% by moles of the overall content of organic groups.

A semiconductor silicon wafer was coated with this silicone varnish in a coating thickness of about 0.5 μm as dry and prebaked at 150° C. for 30 minutes followed by irradiation with electron beams of 20 kV. The sensitivity of the resin film for radiation-induced curing was sufficiently high. Further, the silicon wafer coated with the resin was subjected to a test of the etching velocity by the reactive ion etching using oxygen and carbon tetrafluoride as the etching gas. The results were that the velocity was substantially zero when the etching was performed in an oxygen plasma under a pressure of 100 mmHg with a power input of 0.5 watt/$cm^2$ and the velocity was 0.7 nm per minute when the etching was performed in an carbon tetrafluoride plasma under a pressure of 20 mmHg and with the same power input as above.

What is claimed is:

1. 4-Chloromethylphenyl methyl dichlorosilane.
2. A method for the preparation of 4-chloromethylphenyl methyl dichlorosilane which comprises chlorinating 4-tolyl methyl dichlorosilane with sulfuryl chloride as a chlorinating agent.

* * * * *